(12) United States Patent
Umemoto

(10) Patent No.: US 7,557,311 B2
(45) Date of Patent: Jul. 7, 2009

(54) BODY MEASURING DEVICE HAVING INDIVIDUAL OUTPUT FORMAT CUSTOMIZATION FEATURE

(75) Inventor: Eiichi Umemoto, Tsurugashima (JP)

(73) Assignee: Tanita Corporation, Tokyo (JP)

( * ) Notice: Subject to any disclaimer, the term of this patent is extended or adjusted under 35 U.S.C. 154(b) by 39 days.

(21) Appl. No.: 11/889,824

(22) Filed: Aug. 16, 2007

(65) Prior Publication Data
US 2008/0073128 A1 Mar. 27, 2008

(30) Foreign Application Priority Data
Sep. 25, 2006 (JP) .............. 2006-259528
May 31, 2007 (JP) .............. 2007-144548

(51) Int. Cl.
G01G 19/40 (2006.01)
A61B 5/053 (2006.01)

(52) U.S. Cl. .................. 177/25.16; 177/25.19; 600/547

(58) Field of Classification Search ................ 600/547; 177/25.16, 25.19
See application file for complete search history.

(56) References Cited

U.S. PATENT DOCUMENTS

| 6,354,996 | B1 * | 3/2002 | Drinan et al. ............... 600/300 |
| 6,539,310 | B2 * | 3/2003 | Shimomura ................. 600/300 |
| 6,989,494 | B2 * | 1/2006 | Yagioka et al. .......... 177/25.13 |
| 7,075,537 | B2 * | 7/2006 | Simond et al. ........... 345/440.2 |
| 2001/0050683 | A1 | 12/2001 | Ishikawa et al. |
| 2002/0013521 | A1 * | 1/2002 | Baba et al. ................. 600/301 |

FOREIGN PATENT DOCUMENTS

| EP | 1 086 650 A1 | 3/2001 |
| EP | 1 671 583 A1 | 6/2006 |
| JP | 2001-204703 | 7/2001 |
| WO | WO 99/52425 | 10/1999 |

OTHER PUBLICATIONS

European Search Report issued in European Patent Application No. EP 07 01 8386, mailed Jan. 23, 2008.

* cited by examiner

*Primary Examiner*—Randy W Gibson
(74) *Attorney, Agent, or Firm*—McDermott Will & Emery LLP

(57) ABSTRACT

There is provided a body measuring device with an individual output format customization feature which can provide information of measurement results in an output format desired by each individual.

The body measuring device customizes an output format for each individual in advance by individual output format customization means 3, starts a measurement by individual measurement start means 1, measures a body indicator for each individual by body measurement means 2, and outputs the result of measurement of the body indicator for each individual in the output format customized for each individual in advance by individual measurement result output means 4.

11 Claims, 19 Drawing Sheets

FIG.6

"SELECT MEASUREMENT START KEY TO CORRESPOND
TO PHYSICAL FEATURES AND OUTPUT FORMAT."

MEASUREMENT START KEY No. : 5

FIG.7

"ENTER PHYSICAL FEATURES."

SEX     FEMALE

AGE     1 8 YEARS OLD

HEIGHT  1 6 0 cm

FIG.8

"DEFINE OUTPUT FORMAT."

| DISPLAY: NEEDED | VOICE: NEEDED |
|---|---|
| LETTER SIZE : SMALL | VOICE VOLUME: MEDIUM |
| LETTER COLOR: BLACK | SEX : FEMALE |
| DECORATION : <u>NEEDED</u> | LANGUAGE :JAPANESE |
| DISPLAY ITEMS: 4 | VOICE ITEMS: 2 |
| LANGUAGE :JAPANESE | |
| GRAPH : NEEDED | |
| ADVICE : NEEDED | |

FIG.9
"SELECT TYPE OF DECORATION."
(a) 
(b) 
(c) 
(d) 

FIG.11
"SELECT TYPE OF GRAPH."
LINE
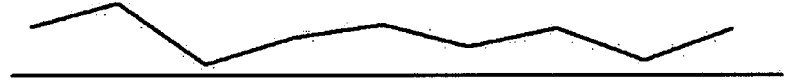
BAR

BODY WEIGHT (kg)

61.8

MUSCLE MASS (kg)

36.1

(b)

BODY FAT PERCENTAGE (%)

22.6

BASAL METABOLIC RATE (kcal/days)

1700

INTERNAL BODY AGE (YEARS OLD)

38

(c)

BODY WEIGHT (kg)

44.8

(d)

| BODY WEIGHT (kg) | BODY FAT PERCENTAGE (%) |
|---|---|
| 60.0 | 20.2 |
| BASAL METABOLIC RATE (kcal/days) | BONE MASS (kg) |
| 1810 | 4.0 |
| VISCERAL FAT LEVEL | BODY WATER CONTENT (kg) |
| 6 | 45.6 |
| MUSCLE MASS (kg) | INTERNAL BODY AGE (YEARS OLD) |
| 35.8 | 22 |

(e)

| BODY WEIGHT (kg) | BODY FAT PERCENTAGE (%) |
|---|---|
| 48.0 | 22.6 |
| BASAL METABOLIC RATE (kcal/days) | BONE MASS (kg) |
| 1740 | 3.2 |

BODY MEASURING DEVICE HAVING INDIVIDUAL OUTPUT FORMAT CUSTOMIZATION FEATURE

BACKGROUND OF THE INVENTION (i) Field of the Invention

This invention relates to a body measuring device with an individual output format customization feature which performs a measurement on the bodies of multiple subjects individually and outputs the result of the measurement in an output format specific to each individual.

(ii) Description of the Related Art

A body measuring device which can be used by a number of subjects comprises a plurality of personal keys which correspond to the respective subjects, measures the body of a subject by the operation of this personal key and displays the measurement results (measurement values, graph or registered physical features) in the same display format regardless of which personal key has operated (for example, refer to Patent Publication 1).

Patent Publication 1

Japanese Patent Laid-Open Publication No. 2001-204703

However, since the conventional body measuring device displays measurement results in the same display format regardless of user, users have a problem that displayed characters are too small to read comfortably, displayed information is difficult to understand because it includes unnecessary information, and they do not notice having made a measurement using someone else's personal key.

Thus, an object of the present invention is to solve the above problems of the prior art and provide a body measuring device with an individual output format customization feature which can provide information of measurement results in an output format desired by each individual.

SUMMARY OF THE INVENTION

A body measuring device having an individual output format customization feature according to the present invention comprises:

individual measurement start means, body measurement means, individual output format customization means, and individual measurement result output means, wherein the individual measurement start means starts measurement of body indicator for each individual, the body measurement means measures a body indicator for each individual based on the start by the individual measurement start means, the individual output format customization means customizes, for each individual, an output format for the result of measurement of the body indicator for each individual by the body measurement means, and the individual measurement result output means outputs the result of measurement of the body indicator for each individual by the body measurement means, in the output format customized for each individual by the individual output format customization means.

Further, the individual measurement start means comprises:

a plurality of measurement start keys which operate individually, and a measurement start control section which starts measurement of body indicator for each individual based on the operation of each measurement start key, the individual output format customization means comprises:

setting keys which set the measurement start keys used by individuals and output formats desired by the individuals, a correspondence relationship setting control section which sets correspondence relationships between the measurement start keys used by the individuals and the output formats desired by the individuals which have been set by the setting keys, and a correspondence relationship storage section which stores the correspondence relationships set by the correspondence relationship setting control section, and the individual measurement result output means comprises:

a measurement result output control section which selects an output format corresponding to a measurement start key which has caused the measurement start control section to start measurement of body indicator and controls output of the result of measurement of the body indicator in the selected output format, and a measurement result output section which outputs the result of measurement of the body indicator under the control of the measurement result output control section.

Further, the output format includes a display item and/or a voice item, and the body measurement means measures only a body indicator associated with a display item and/or a voice item which have/has been set by the setting keys.

The body measuring device having an individual output format customization feature according to the present invention customizes an output format for each individual in advance by the individual output format customization means (setting keys, correspondence relationship setting control section and correspondence relationship storage section), starts a measurement by the individual measurement start means (measurement start keys and measurement start control section), measures a body indicator for each individual by the body measurement means, and outputs the result of measurement of the body indicator for each individual in the output format customized for each individual in advance by the individual measurement result output means (measurement result output control section and measurement result output section). Therefore, information about measurement results can be obtained in an output format desired by each individual.

Further, since the body measurement means measures only a body indicator associated with a display item and/or a voice item which have/has been set by the setting keys, each individual can make a measurement in minimum measurement time, thereby preventing the users from feeling frustrated during measurement.

BRIEF DESCRIPTION OF THE DRAWINGS

FIG. 6 is a measurement start key setting screen diagram which illustrates a screen at the time of setting of measurement start key of the body measuring device having an individual output format customization feature (Examples 1, 2, 3, 4).

FIG. 7 is a physical feature setting screen diagram which illustrates a screen at the time of setting of physical features in the body measuring device having an individual output format customization feature (Examples 1, 2, 3, 4).

FIG. 8 is an output format setting screen diagram which illustrates a screen at the time of setting of output format in the body measuring device having an individual output format customization feature (Examples 1, 2, 3, 4).

FIG. 9 is a decoration type setting screen diagram which illustrates a screen at the time of setting of decoration in the body measuring device having an individual output format customization feature (Examples 1, 2, 3, 4).

FIG. 11 is a graph setting screen which illustrates a screen at the time of setting of graph in the body measuring device having an individual output format customization feature (Examples 1, 2, 3, 4).

FIG. 13 shows measurement result screens which illustrate screens at the time of display of measurement results in the body measuring device having an individual output format customization feature (Examples 1, 2, 3, 4).

DETAILED DESCRIPTION OF THE PREFERRED EMBODIMENTS

Figure 1:
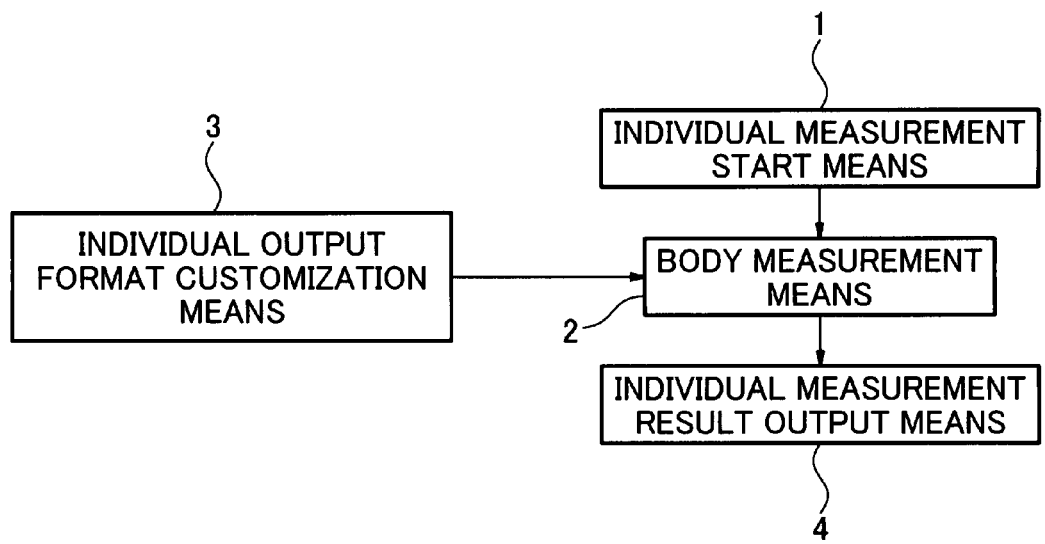
FIG. 1 is a functional block diagram which functionally illustrates the constitution of a body measuring device having an individual output format customization feature.

The configuration of a body measuring device having an individual output format customization feature according to the present invention will be described by use of a functional block diagram shown in FIG. 1. The body measuring device having an individual output format customization feature according to the present invention comprises individual measurement start means 1, body measurement means 2, individual output format customization means 3 and individual measurement result output means 4. The body measuring device performs a measurement on the bodies of multiple subjects individually and outputs the result of the measurement in an output format specific to each individual.

The individual measurement start means 1 starts measurement of body indicator for each individual. In other words, the means 1 comprises a plurality of starting devices which are activated individually for measurement of body indicator. In the present invention, body indicators refer to indicators which indicate forms, components or conditions in a body (e.g. values of body weight, body fat, visceral fat, muscles, body water, basal metabolism, bones, internal body age, blood pressure and height).

The body measurement means 2 measures a body indicator for each individual based on the start of measurement of body indicator for each individual by the individual measurement start means 1. In other words, the means 2 measures a body indicator for each individual based on activation of each starting device.

The individual output format customization means 3 customizes, for each individual, an output format for the result of measurement of the body indicator for each individual by the body measurement means 2. In other words, the means 3 sets an output format desired by each individual, for the result of measurement of the body indicator for each individual which is obtained by measurement based on activation of each starting device.

The individual measurement result output means 4 outputs the result of measurement of the body indicator for each individual which has been made by the body measurement means 2, in the output format customized for each individual by the individual output format customization means 3. In other words, the means 3 outputs the result of measurement of each body indicator which has been made based on activation of each starting device, in the output format desired by each individual.

The thus constituted body measuring device having an individual output format customization feature customizes an output format for each individual in advance by the individual output format customization means 3, starts a measurement by the individual measurement start means 1, measures a body indicator for each individual by the body measurement means 2, and outputs the result of measurement of the body indicator for each individual in the output format customized for each individual in advance by the individual measurement result output means 4. Therefore, information about measurement results can be obtained in an output format desired by each individual.

Hereinafter, examples in the above-described configuration will be described specifically.

Example 1

Figure 2:
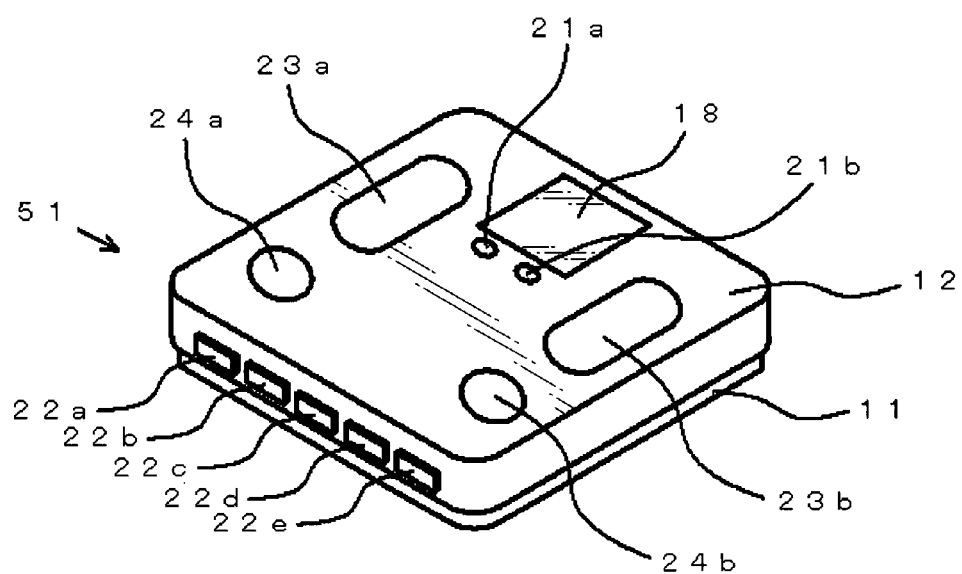
FIG. 2 is an external view of a body measuring device having an individual output format customization feature (Example 1).
Figure 3:
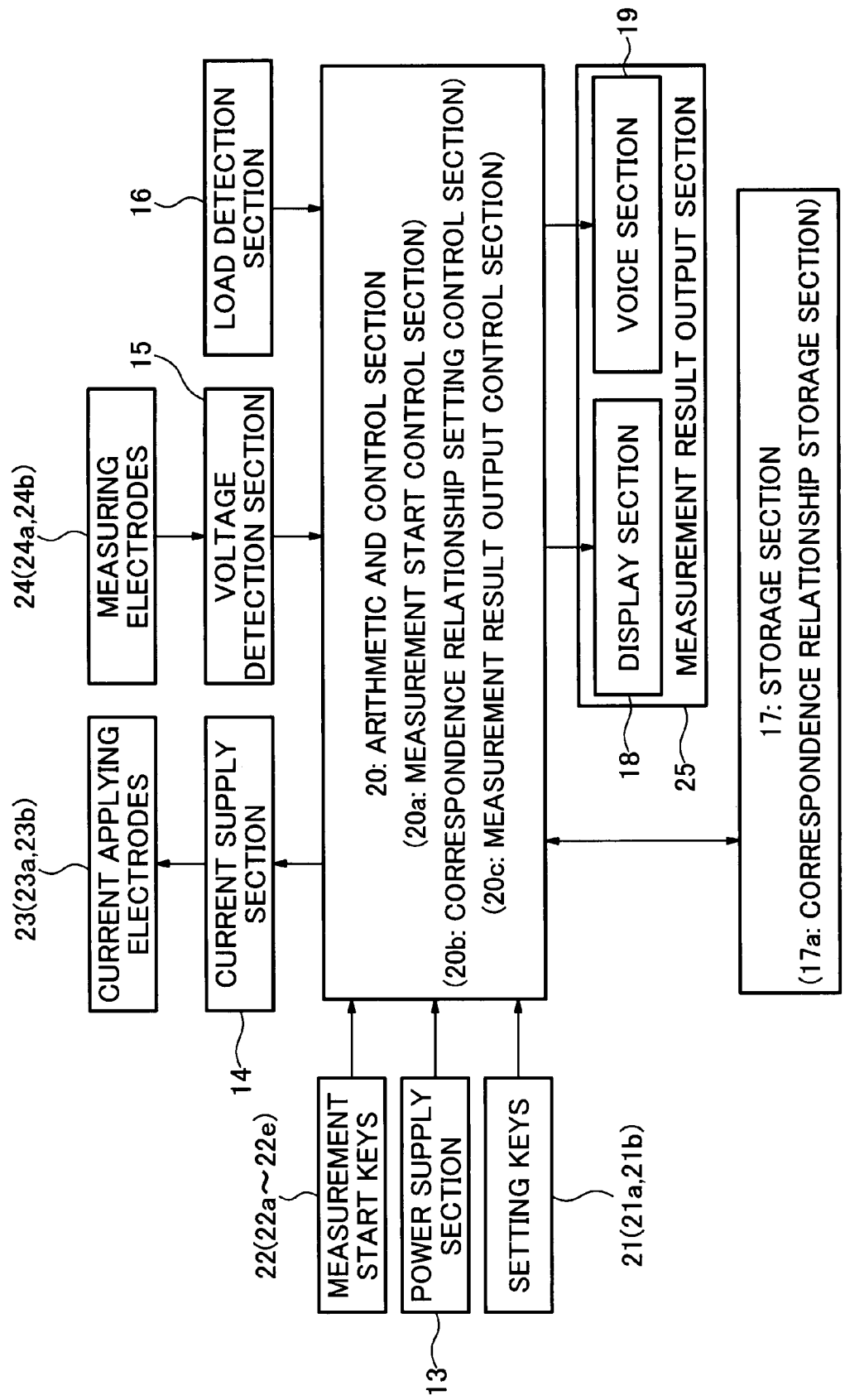
FIG. 3 is a main part block diagram which illustrates main parts constituting the body measuring device having an individual output format customization feature (Example 1).

First, the specific constitution of a body measuring device 51 having an individual output format customization feature in the present example will be described by primarily using an external view shown in FIG. 2 and a main part block diagram shown in FIG. 3.

The body measuring device 51 with an individual output format customization feature in the present example 1 comprises a base 11 and a platform 12. In the base 11 and platform 12, there are provided a power supply section 13, a current supply section 14, a voltage detection section 15, a load detection section 16, a storage section 17 (correspondence relationship storage section 17a), a voice section 19, and an arithmetic and control section 20 (measurement start control section 20a, correspondence relationship setting control section 20b, measurement result output control section 20c). On the external surface of the platform 12, setting keys 21, measurement start keys 22, a display section 18, current applying electrodes 23 and measuring electrodes 24 are provided.

The power supply section 13 supplies electric power to each of the sections in the electrical system of the present device.

The setting keys 21 comprise a selection key 21a and an enter key 21b. The setting keys 21 cause the power supply section 13 to start supplying power for settings and make settings for the measurement start keys used by individuals and output formats desired by the individuals. Further, the setting keys 21 also make settings for the physical features of the individuals. More specifically, the settings of the measurement start keys are made by selecting and entering allocated numbers (Nos. 1 to 5). Meanwhile, the settings of the output formats are made by selecting whether display is needed and whether voice is needed and entering the selections. When display is needed, letter size (large, medium, small), letter color (black, red, blue, orange, green), decoration (needed or not needed; if needed, decorations a to d), display items (body fat percentage, body weight, visceral fat level, muscle mass, body water content, basal metabolic rate, bone mass, internal body age), language (Japanese, English, French, German, Chinese, Korean), graph (line, bar) and advice (needed or not needed) are selected and entered. When voice is needed, voice volume (large, medium, small), gender (male, female), language (Japanese, English, French, German, Chinese, Korean) and voice items (body fat percentage, body weight, visceral fat level, muscle mass, body water content, basal metabolic rate, bone mass, internal body age) are selected and entered. Further, the settings of the physical features are made by selecting and entering gender (male, female), age (0 to 100) and height (10 to 250 cm).

The measurement start keys 22 comprise a plurality of keys 22a, 22b, 22c, 22d and 22e. These keys operate individually. Their individual operation causes the power supply section 13 to start supplying power for measurement.

The current supply section 14 generates a current between the current applying electrodes under the control of the arithmetic and control section 20 to pass the current through a body. The voltage detection section 15 detects a voltage generated between the measuring electrodes when a current is passed between the current applying electrodes.

The current applying electrodes 23 comprise a pair of electrodes 23a and 23b and are terminals for passing a current through a body. The measuring electrodes 24 comprise a pair of electrodes 24a and 24b and are terminals for detecting a voltage generated when a current is passed between the current applying electrodes.

The load detection section 16 comprises a weight sensor, a voltage amplifier and an A/D converter and detects a voltage generated based on a load (body weight) imposed when a subject stands on the platform 12.

The display section 18 displays items associated with settings made by the setting keys 21 and displays the measurement results of body indicators (body weight value, body fat percentage, visceral fat level, muscle mass, body water content, basal metabolic rate, bone mass, internal body age) calculated by the arithmetic and control section 20 in a predetermined output format.

The voice section 19 reads out the measurement results of body indicators (body weight value, body fat percentage, visceral fat level, muscle mass, body water content, basal metabolic rate, bone mass, internal body age) calculated by the arithmetic and control section 20 in a predetermined output format.

The display section 18 and the voice section 19 constitute a measurement result output section 25.

The storage section 17 also serves as the correspondence relationship storage section 17a and stores information associated with settings, measurements, calculations and display.

The correspondence relationship storage section 17a stores correspondence relationships between the measurement start keys 22 used by individuals and output formats desired by the individuals and correspondence relationships between the measurement start keys 22 used by the individuals and the physical features of the individuals. The correspondence relationships are set by the correspondence relationship setting control section 20b which will be described later.

The arithmetic and control section 20 also serves as the measurement start control section 20a, correspondence relationship setting control section 20b and measurement result output control section 20c. The arithmetic and control section 20 (i) controls setting of physical features by the setting keys 21, (ii) calculates and controls a bioelectrical impedance based on a current generated from the current supply section 14 and a voltage detected by the voltage detection section 15 upon passage of the current, (iii) calculates and controls a body weight based on a detection signal from the load detection section 16, (iv) selects physical features corresponding to a measurement start key 22 which has caused the measurement start control section 20a to start measurement of body indicator from the correspondence relationships between the measurement start keys 22 used by the individuals and the physical features of the individuals and calculates and controls body indicators (body weight value, body fat percentage, visceral fat level, muscle mass, body water content, basal metabolic rate, bone mass, internal body age) based on the selected physical features and the calculated bioelectrical impedance, and (v) calculates and controls various other information.

The measurement start control section 20a starts measurement of body indicator for each individual based on operation of each measurement start key 22. The correspondence relationship setting control section 20b sets correspondence relationships between the measurement start keys 22 used by individuals and output formats desired by the individuals which have been set by the setting keys 21 and sets correspondence relationships between the measurement start keys 22 used by individuals and the physical features of the individuals. The measurement result output control section 20c selects an output format corresponding to a measurement start key 22 which has caused the measurement start control section 20a to start measurement of body indicator from the correspondence relationships between the measurement start keys 22 used by individuals and the output formats desired by the individuals which have been stored in the correspondence relationship storage section 17a and controls output of the result of measurement of the body indicator in the selected output format.

The measurement start keys 22 and the measurement start control section 20a constitute the individual measurement start means 1. Further, the setting keys 21, the correspondence relationship setting control section 20b and the correspondence relationship storage section 17a constitute the individual output format customization means 3. In addition, the measurement result output control section 20c and the measurement result output section 25 constitute the individual measurement result output means 4.

Figure 4:
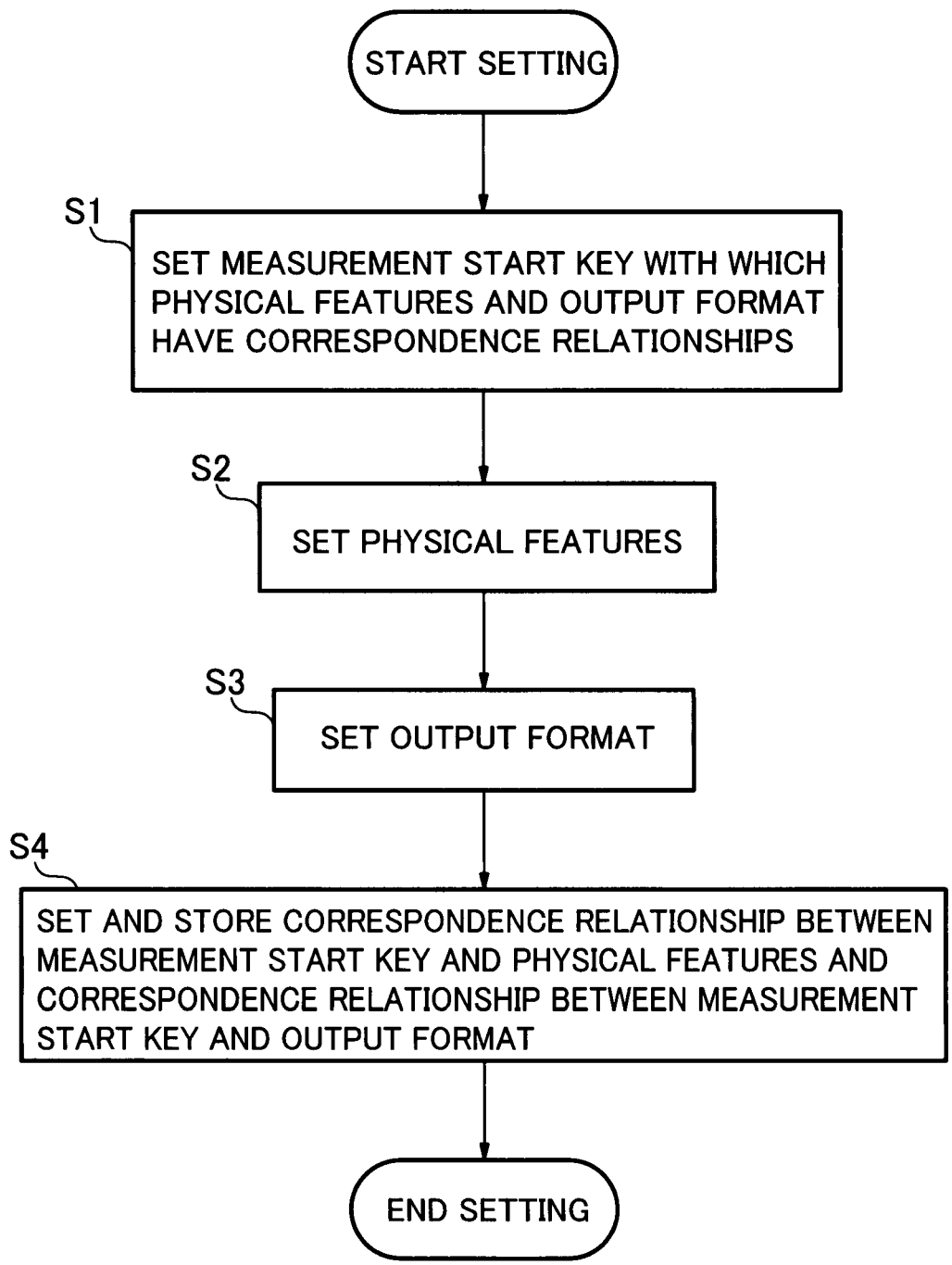
FIG. 4 is a setting flowchart which illustrates operational procedures at the time of setting of the body measuring device having an individual output format customization feature (Examples 1, 2, 3, 4).

Next, the operations of the body measuring device 51 with an individual output format customization feature in the present example 1 will be described by primarily using a setting flowchart shown in FIG. 4.

First, when the enter key 21b is pressed, the power supply section 13 supplies electric power to each of the sections in the electrical system, and the display section 18 displays such a measurement start key setting screen as shown in FIG. 6. On the measurement start key setting screen, under the control of the arithmetic and control section 20, a cursor is positioned in the allocated number field of the measurement start keys, the numeric value is switched from "1" to "5" in turn each time the selection key 21a is pressed, and one of the numeric values "1" to "5" which is displayed over the cursor is entered when the enter key 21b is pressed (STEP S1).

Then, the display section 18 displays a physical feature setting screen as shown in FIG. 7. On the physical feature setting screen, under the control of the arithmetic and control section 20, a cursor is first positioned in the gender field, "female" and "male" are displayed alternately each time the selection key 21a is pressed, "female" or "male" which is displayed over the cursor is entered when the enter key 21b is pressed, and the cursor is moved to the age field. Then, the numeric value is switched from "0" to "100" in turn each time the selection key 21a is pressed, one of the numeric values "0" to "100" which is displayed over the cursor is entered when the enter key 21b is pressed, and the cursor is moved to the height field. Then, the numeric value is switched from "10" to "250" in turn each time the selection key 21a is pressed, and one of the numeric values "10" to "250" which is displayed over the cursor is entered when the enter key 21b is pressed. Then, the storage section 17 stores these entered physical features (STEP S2).

Then, the display section 18 displays an output format setting screen as shown in FIG. 8. On the output format setting screen, under the control of the arithmetic and control section 20, a cursor is first positioned in the display field, "needed" and "not needed" are displayed alternately each time the selection key 21a is pressed, and "needed" or "not needed" which is displayed over the cursor is entered when the enter key 21b is pressed. Then, when "needed" has been entered, the cursor is moved to the letter size field, while when "not needed" has been entered, the cursor is moved to the voice field.

Then, when the cursor has been moved to the letter size field, "large", "medium" and "small" are displayed in turn each time the selection key 21a is pressed, "large", "medium" or "small" which is displayed over the cursor is entered when the enter key 21b is pressed, and the cursor is moved to the letter color field.

Then, "black", "red", "blue", "orange" and "green" are displayed in turn each time the selection key 21a is pressed, "black", "red", "blue", "orange" or "green" which is displayed over the cursor is entered when the enter key 21b is pressed, and the cursor is moved to the decoration field.

Then, "needed" and "not needed" are displayed alternately each time the selection key 21a is pressed, and "needed" or "not needed" which is displayed over the cursor is entered when the enter key 21b is pressed. Then, when "needed" has been entered, a decoration type setting screen as shown in FIG. 9 is displayed, while when "not needed" has been entered, the cursor is moved to the display item field.

Then, on the decoration type setting screen, the cursor is positioned around the currently selected item, the position of the cursor is moved among "decoration a", "decoration b", "decoration c" and "decoration d" in turn each time the selection key 21a is pressed, "decoration a", "decoration b", "decoration c" or "decoration d" which is surrounded by the cursor is entered when the enter key 21b is pressed, and the cursor is moved to the display item field on the output format setting screen.

Figure 10:
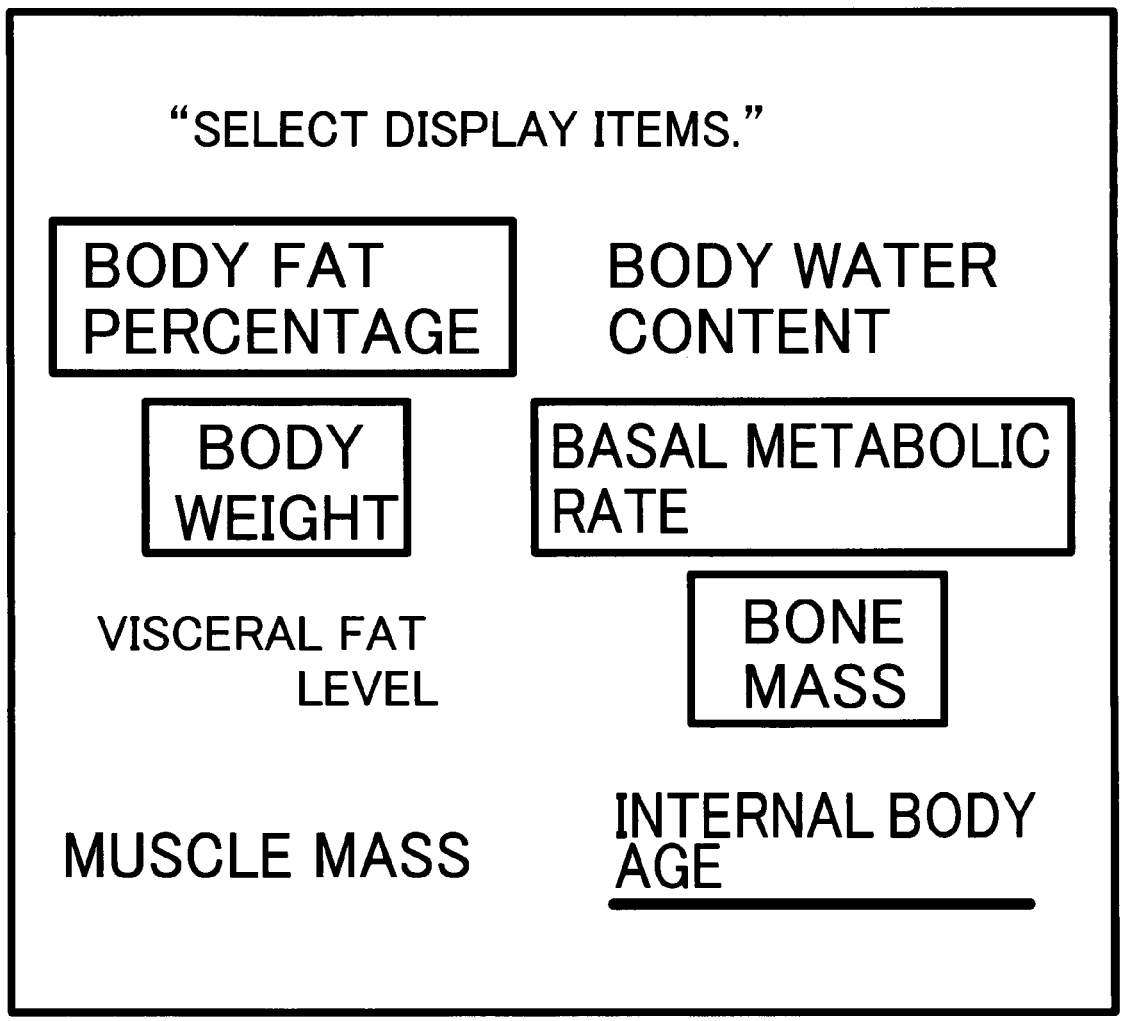
FIG. 10 is a display item setting screen which illustrates a screen at the time of setting of display item in the body measuring device having an individual output format customization feature (Examples 1, 2, 3, 4).

Then, when the selection key 21a is pressed, a display item setting screen as shown in FIG. 10 is displayed. On the display item setting screen, the cursor is first positioned at "body fat percentage" and then moved to "body weight", "visceral fat level", "muscle mass", "body water content", "basal metabolic rate", "bone mass" and "internal body age" in this order each time the selection key 21a is pressed, and when the enter key 21b is pressed during this operation, an item surrounded by the cursor at that time is entered. Then, when the selection key 21a is pressed with the cursor positioned at "internal body age", the cursor on the output format setting screen is moved to the language field. Further, at that time, the number of items entered on the display item setting screen is displayed in the display item field on the output format setting screen.

Then, "Japanese", "English", "French", "German", "Chinese" and "Korean" are displayed in turn each time the selection key 21a is pressed, "Japanese", "English", "French", "German", "Chinese" or "Korean" which is displayed over the cursor is entered when the enter key 21b is pressed, and the cursor is moved to the graph field.

Then, "needed" and "not needed" are displayed alternately each time the selection key 21a is pressed, and "needed" or "not needed" which is displayed over the cursor is entered when the enter key 21b is pressed. Then, when "needed" has been entered, a graph setting screen as shown in FIG. 11 is displayed, while when "not needed" has been entered, the cursor is moved to the advice field.

Then, on the graph setting field, the cursor is positioned around the currently selected item, the position of the cursor is moved from "line" to "bar" or vice versa each time the selection key 21a is pressed, "line" or "bar" which is surrounded by the cursor is entered when the enter key 21b is pressed, and the cursor is moved to the advice field on the output format setting screen.

Then, when the cursor has been moved to the advice field, "needed" and "not needed" are displayed alternately each time the selection key 21a is pressed, "needed" or "not needed" which is displayed over the cursor is entered when the enter key 21b is pressed, and the cursor is moved to the voice field.

Then, when the cursor has been moved to the voice field, "needed" and "not needed" are displayed alternately each time the selection key 21a is pressed, and "needed" or "not needed" which is displayed over the cursor is entered when the enter key 21b is pressed. Then, when "needed" has been entered, the cursor is moved to the voice volume field, while when "not needed" has been entered, the setting of the output format is ended (STEP S3).

Then, when the cursor has been moved to voice volume field, "large", "medium" and "small" are displayed in turn each time the selection key 21a is pressed, "large", "medium" or "small" which is displayed over the cursor is entered when the enter key 21b is pressed, and the cursor is moved to the gender field.

Then, "female" and "male" are displayed alternately each time the selection key 21a is pressed, "female" or "male" which is displayed over the cursor is entered when the enter key 21b is pressed, and the cursor is moved to the language field.

Then, "Japanese", "English", "French", "German", "Chinese" and "Korean" are displayed in turn each time the selection key 21a is pressed, "Japanese", "English", "French", "German", "Chinese" or "Korean" which is displayed over the cursor is entered when the enter key 21b is pressed, and the cursor is moved to the voice item field.

Figure 12:
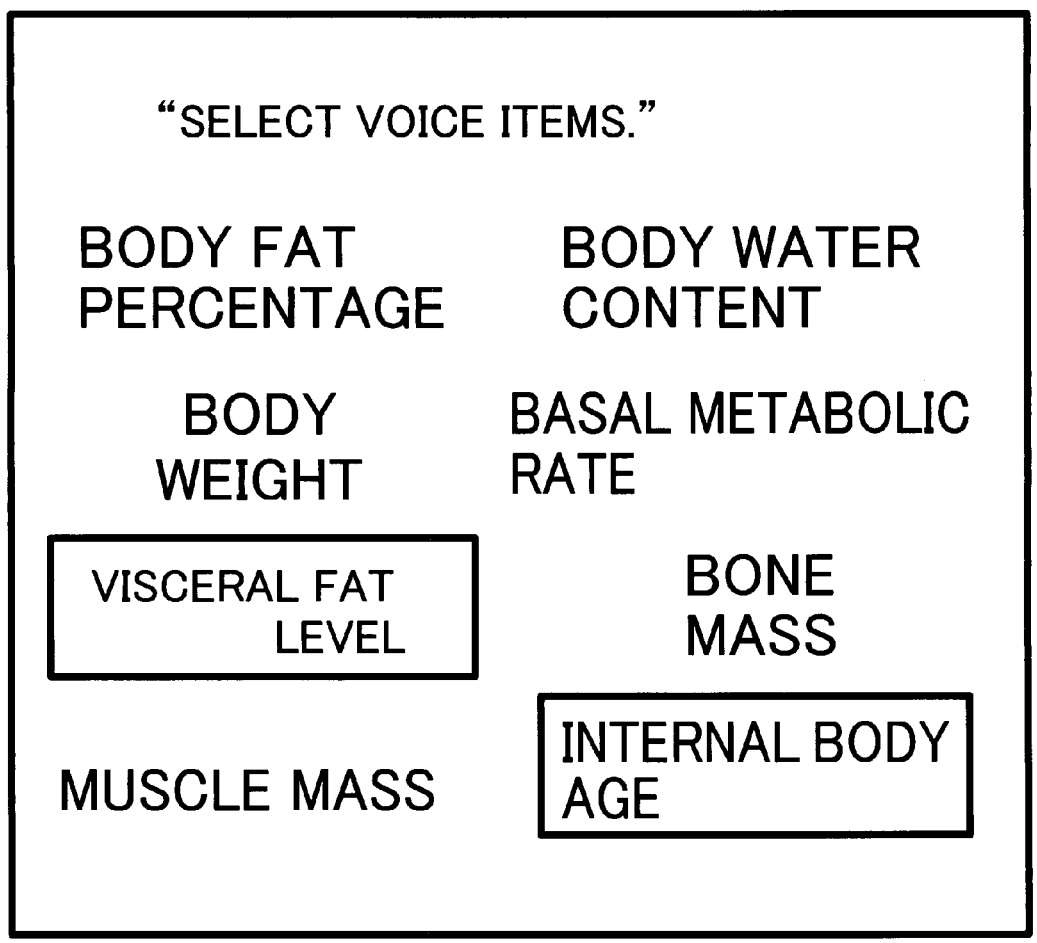
FIG. 12 is a voice item setting screen which illustrates a screen at the time of setting of voice item in the body measuring device having an individual output format customization feature (Examples 1, 2, 3, 4).

Then, when the selection key 21a is pressed, a voice item setting screen as shown in FIG. 12 is displayed. On the voice item setting screen, the cursor is first positioned at "body fat percentage" and then moved to "body weight", "visceral fat level", "muscle mass", "body water content", "basal metabolic rate", "bone mass" and "internal body age" in this order each time the selection key 21a is pressed, and when the enter key 21b is pressed during this operation, an item surrounded by the cursor at that time is entered. Then, when the selection key 21a is pressed with the cursor positioned at "internal body age", the setting of the output format is ended. Further, at that time, the number of items entered on the voice item setting screen is displayed in the voice item field on the output format setting screen (STEP S3).

Then, when the setting of the output format is ended, the correspondence relationship setting control section 20b sets a correspondence relationship between the allocated number set in STEP S1 and the physical features set in STEP S2, and the correspondence relationship storage section 17a stores the correspondence relationship between the allocated number and the physical features. Further, the correspondence relationship setting control section 20b sets a correspondence relationship between the allocated number set in STEP S1 and the output format set in STEP S3, and the correspondence relationship storage section 17a stores the correspondence relationship between the allocated number and the output format (STEP S4), thereby ending a series of settings.

Figure 5:
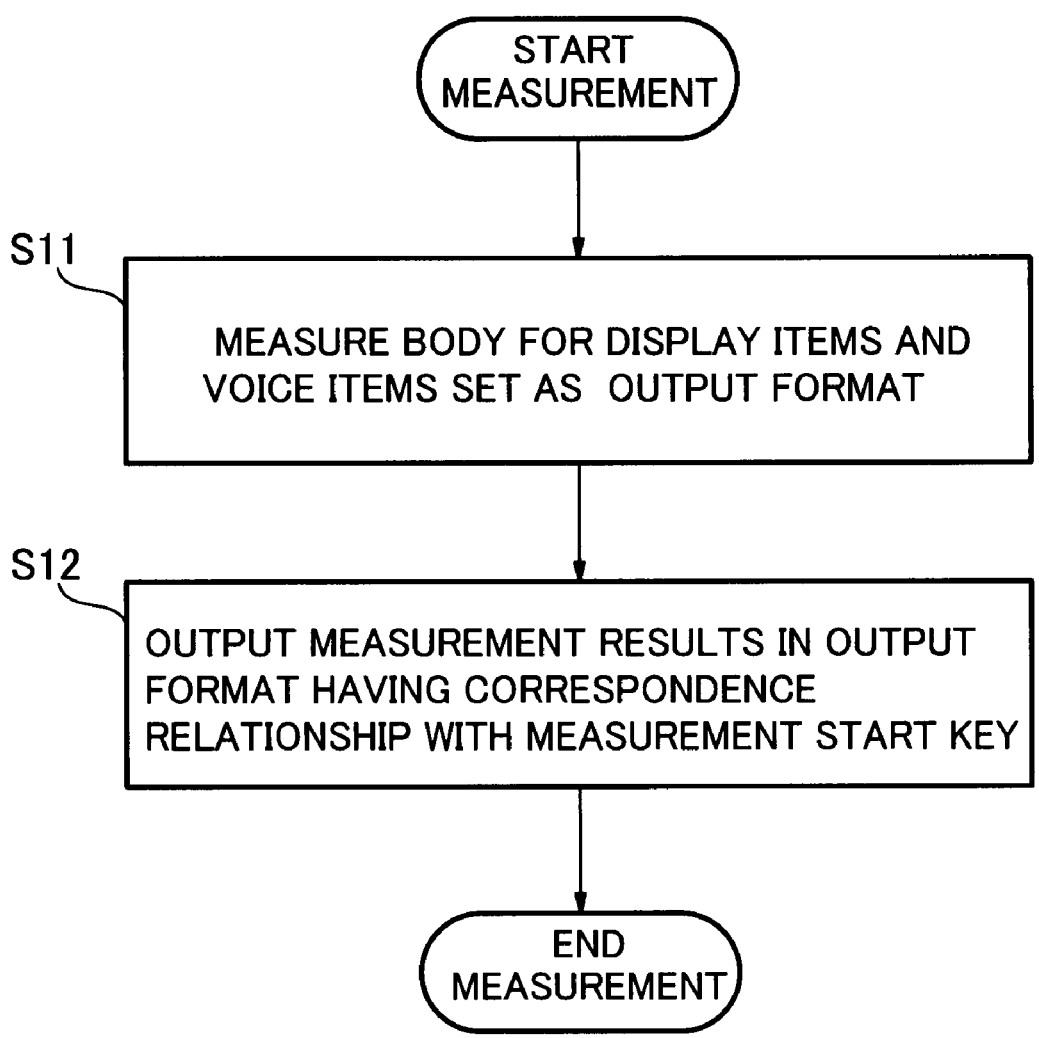
FIG. 5 is a measurement flowchart which illustrates operational procedures at the time of measurement by the body measuring device having an individual output format customization feature (Examples 1, 2, 3, 4).

Next, the operations of the body measuring device having an individual output format customization feature in the present example will be described by primarily using a measurement flowchart shown in FIG. 5.

First, when the measurement start key 22 which has been set for a subject is pressed, the power supply section 13 supplies electric power to each of the sections in the electrical system. Then, when the subject stands on the platform 12 with the bottom of the left foot in contact with the current applying electrode 23a and the measuring electrode 24a and the bottom of the right foot in contact with the current applying electrode 23b and the measuring electrode 24b, the load detection section 16 detects a voltage generated at that time, the arithmetic and control section 20 calculates the bodyweight of the subject, and the storage section 17 stores the calculated body weight.

Then, the arithmetic and control section 20 calculates a bioelectrical impedance based on a current generated from the current supply section 14 and the voltage detected at that time by the voltage detection section 15 and calculates the body fat percentage, visceral fat level, muscle mass, body water content, basal metabolic rate, bone mass and/or internal body age which have/has been set as the display item(s) and the voice item(s) based on the calculated bioelectrical impedance and physical features corresponding to the allocated number of the measurement start key 22 for the subject from the above stored correspondence relationship between the allocated number and the physical features (STEP S11). For example, when a body fat percentage, body weight, basal metabolic rate and bone mass are set as the display items as shown in FIG. 10 and a visceral fat level and internal body age are set as the voice items as shown in FIG. 12, the body fat percentage, visceral fat level, basal metabolic rate, bone mass and internal body age are calculated.

Then, the measurement result output control section 20c selects an output format corresponding to the allocated number of the measurement start key 22 for the subject from the correspondence relationship between the allocated number and the output format which has been stored in the correspondence relationship storage section 17a and controls the display section 18 and the voice section 19 to output the body fat percentage, body weight, visceral fat level, muscle mass, body water content, basal metabolic rate, bone mass and/or internal body age which have/has been calculated as the display item(s) and the voice item(s) in this selected output format. Then, the display section 18 displays the data under the control of the control section 20c, and the voice section 19 reads out the data under the control of the control section 20c (STEP S12), thereby ending a series of measurements. For example, when the display items and the voice items are set as shown in FIGS. 8, 10 and 12, the display section 18 displays a measurement result screen as shown in FIG. 13(e), and the voice section 19 reads out a visceral fat level and internal body age in Japanese by female voice in a medium tone (i.e. in a tone of casual conversation).

Example 2

Figure 14:
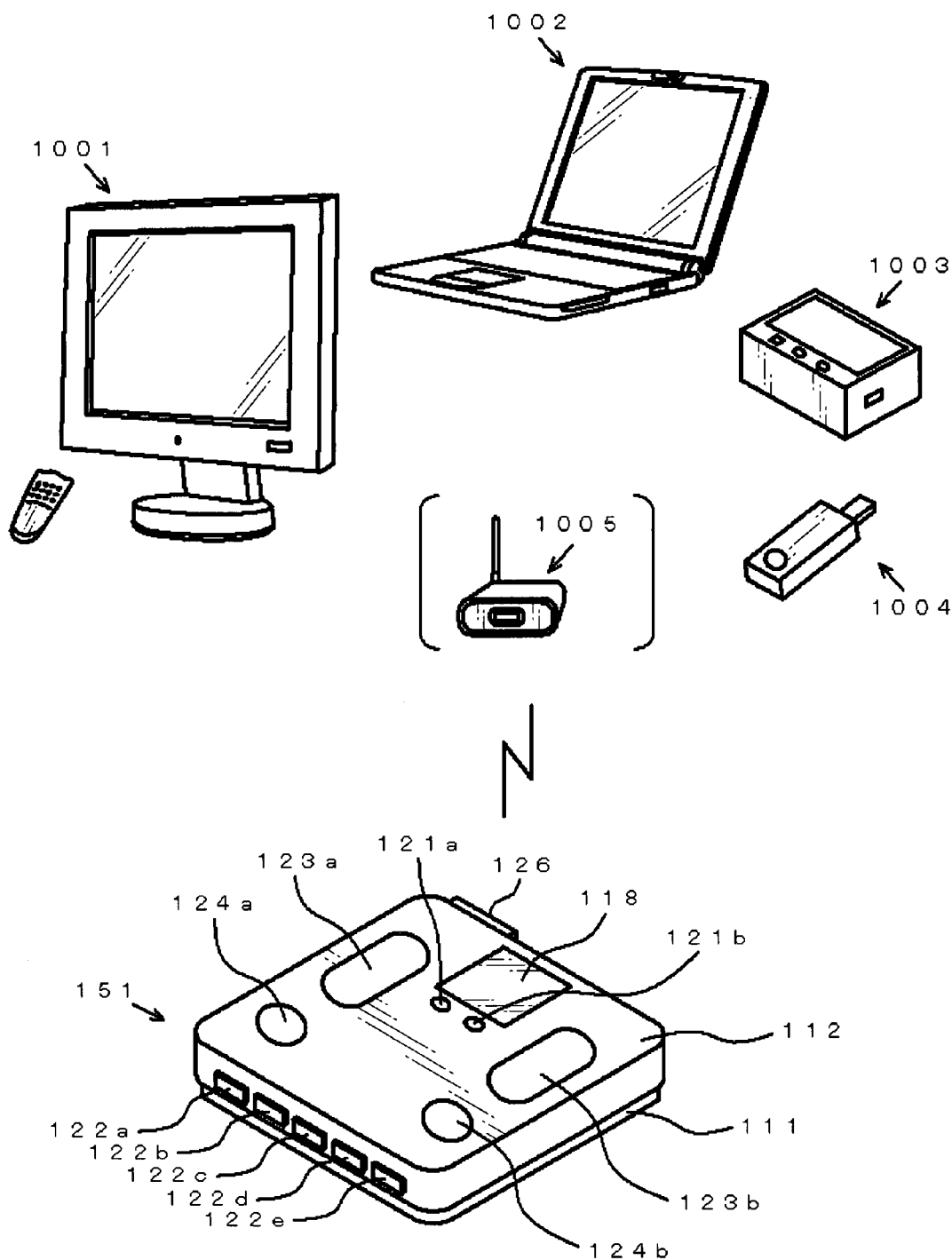
FIG. 14 is an external view of a body measuring device having an individual output format customization feature (Example 2).
Figure 15:
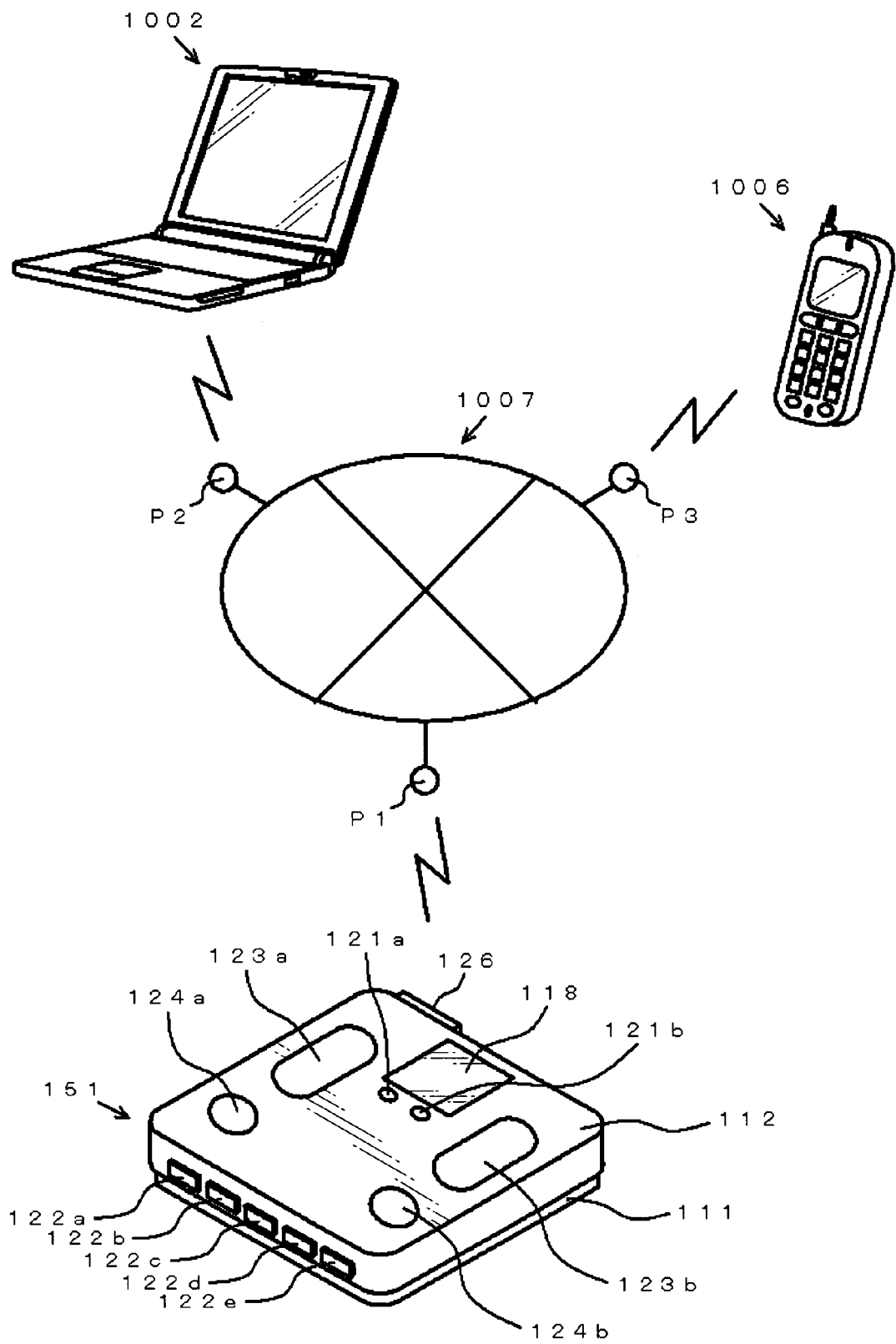
FIG. 15 is an external view of the body measuring device having an individual output format customization feature (Example 2).
Figure 16:
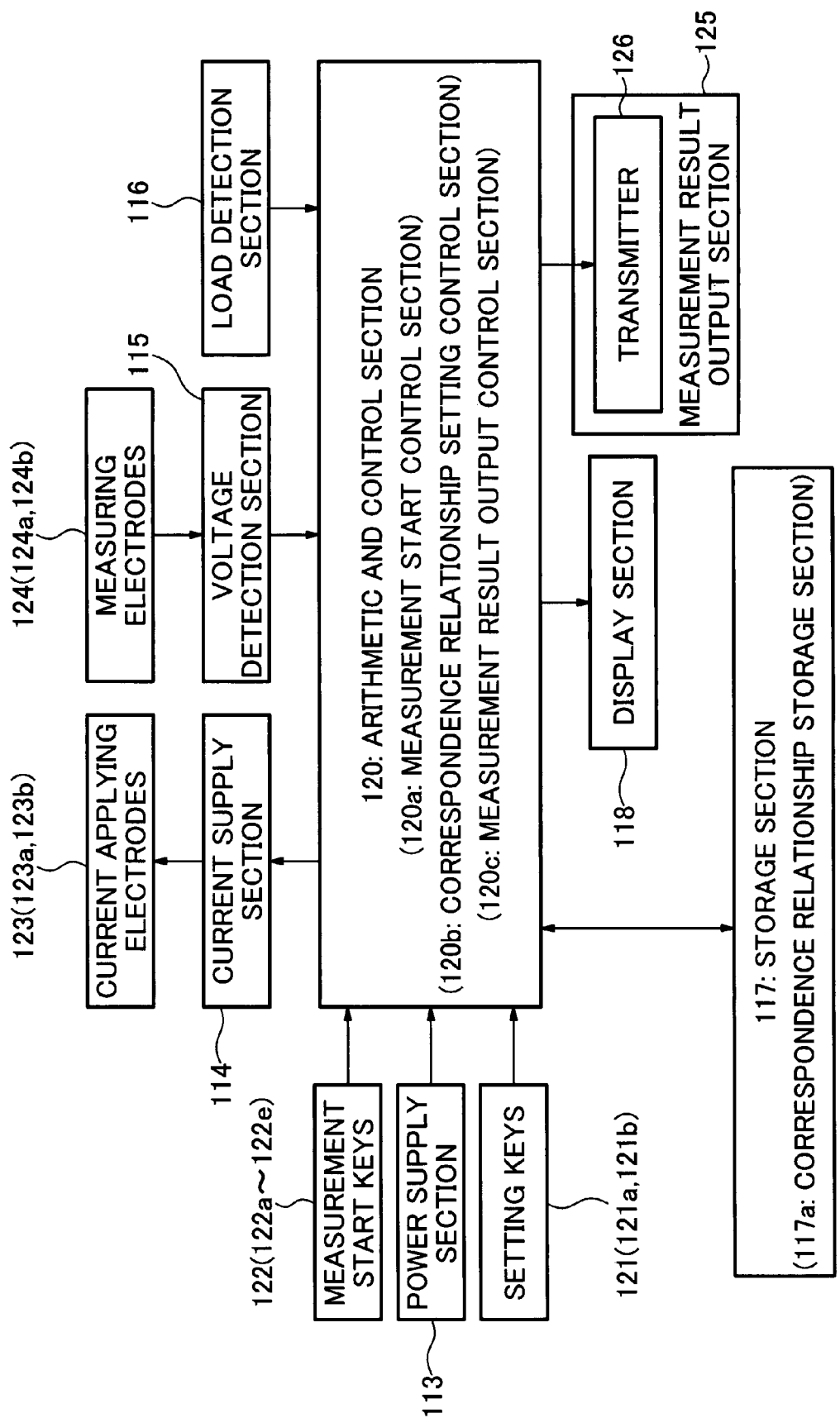
FIG. 16 is a main part block diagram which illustrates main parts constituting the body measuring device having an individual output format customization feature (Example 2).

First, the specific constitution of a body measuring device 151 having an individual output format customization feature in the present example 2 will be described by primarily using an external view shown in FIG. 14, an external view shown in FIG. 15 and a main part block diagram shown in FIG. 16.

The body measuring device 151 with an individual output format customization feature in the present example 2 comprises a base 111 and a platform 112. In the base 111 and platform 112, there are provided a power supply section 113, a current supply section 114, a voltage detection section 115, a load detection section 116, a storage section 117 (correspondence relationship storage section 117a), a display section 118, and an arithmetic and control section 120 (measurement start control section 120a, correspondence relationship setting control section 120b, measurement result output control section 120c). On the external surface of the platform 112, setting keys 121, measurement start keys 122, current applying electrodes 123, measuring electrodes 124, the display section 118 and a transmitter 126 are provided.

The base 111, platform 112, power supply section 113, current supply section 114, voltage detection section 115, load detection section 116, storage section 117 (correspondence relationship storage section 117a), arithmetic and control section 120 (measurement start control section 120a, correspondence relationship setting control section 120b, measurement result output control section 120c), setting keys 121, measurement start keys 122, current applying electrodes 123 and measuring electrodes 124 correspond to the base 11, platform 12, power supply section 13, current supply section 14, voltage detection section 15, load detection section 16, storage section 17 (correspondence relationship storage section 17a), arithmetic and control section 20 (measurement start control section 20a, correspondence relationship setting control section 20b, measurement result output control section 20c), setting keys 21, measurement start keys 22, current applying electrodes 23 and measuring electrodes 24 in Example 1 and serve in the same way as their counterparts in Example 1.

The display section 118 displays items associated with settings made by the setting keys 121.

The transmitter 126 outputs data (signals in a format which can be received by a given external device) for outputting the measurement results of body indicators (body weight value, body fat percentage, visceral fat level, muscle mass, body water content, basal metabolic rate, bone mass, internal body age) calculated by the arithmetic and control section 120 in a predetermined output format to a given external device (device having a display section and a voice section (e.g. a television set 1001, a personal computer 1002, a display/voice instrument 1003, a cellular phone 1006), a device which transfers data to a device having a display section and a voice section (e.g. repeaters 1004, 1005) or a telecommunication network system 1007 which transfers data to a device having a display section and a voice section). In the telecommunication network system 1007 of FIG. 15, P1 and P2 represent a router, and P3 represents a base station.

More specifically, the transmitter 126 comprises a communication section which outputs the data to the external device through radio communication. Under the control of the measurement result output control section 120c, the transmitter 126 (a) transmits the data for outputting the measurement results of the body indicators in a predetermined output format directly to the television set 1001, personal computer 1002 or display/voice instrument 1003 through radio communication or wire communication, (b) transmits the data indirectly through radio communication or wire communication to the repeater 1005 which transfers the data to the television set 1001, personal computer 1002 or display/voice instrument 1003 through radio communication or wire communication, (c) transmits the data indirectly through radio communication, wire communication or connector connection to the repeater 1004 which transfers the data to the television set 1001, personal computer 1002 or display/voice instrument 1003 through connector connection or (d) transmits the data indirectly through radio communication or wire communication to the telecommunication network system 1007 (router P1) which transfers the data to the personal computer 1002 or cellular phone 1006.

The measurement start keys 122 and the measurement start control section 120a constitute the individual measurement start means 1. Further, the setting keys 121, the correspondence relationship setting control section 120b and the correspondence relationship storage section 117a constitute the individual output format customization means 3. In addition, the measurement result output control section 120c and the measurement result output section 125 constitute the individual measurement result output means 4.

Next, the operations of the body measuring device 151 with an individual output format customization feature in the present example 2 will be described. The operations at the time of setting in the present example 2 are the same as those described by use of the setting flowchart of FIG. 4 in the present example 1 except that different reference numbers are allocated to the sections with the same names. Accordingly, descriptions thereof will be omitted.

The operations at the time of measurement in the present example 2 will be described by primarily using the measurement flowchart shown in FIG. 5, as in the description in Example 1.

First, when the measurement start key 122 which has been set for a subject is pressed, the power supply section 113 supplies electric power to each of the sections in the electrical system. Then, when the subject stands on the platform 112 with the bottom of the left foot in contact with the current applying electrode 123a and the measuring electrode 124a and the bottom of the right foot in contact with the current applying electrode 123b and the measuring electrode 124b, the load detection section 116 detects a voltage generated at that time, the arithmetic and control section 120 calculates the body weight of the subject, and the storage section 17 stores the calculated body weight.

Then, the arithmetic and control section 120 calculates a bioelectrical impedance based on a current generated from the current supply section 114 and the voltage detected at that time by the voltage detection section 115 and calculates the body fat percentage, visceral fat level, muscle mass, body water content, basal metabolic rate, bone mass and/or internal body age which have/has been set as the display item(s) and the voice item(s) based on the calculated bioelectrical impedance and physical features corresponding to the allocated number of the measurement start key 122 for the subject from the above stored correspondence relationship between the allocated number and the physical features (STEP S11). For example, when a body fat percentage, body weight, basal metabolic rate and bone mass are set as the display items as shown in FIG. 10 and a visceral fat level and internal body age are set as the voice items as shown in FIG. 12, the body fat percentage, visceral fat level, basal metabolic rate, bone mass and internal body age are calculated.

Then, the measurement result output control section 120c selects an output format corresponding to the allocated number of the measurement start key 122 for the subject from the correspondence relationship between the allocated number and the output format which has been stored in the correspondence relationship storage section 117a and controls the transmitter 126 to output the body fat percentage, body weight, visceral fat level, muscle mass, body water content, basal metabolic rate, bone mass and/or internal body age which have/has been calculated as the display item(s) and the voice item(s) to a given external device in this selected output format. Then, the transmitter 126 outputs the data to the given external device under the control of the control section 120c (STEP S12), thereby ending a series of measurements. Accordingly, for example, when the given external device receives data with the display items and the voice items set as shown in FIGS. 8, 10 and 12, the external device displays a measurement result screen as shown in FIG. 13(e) and can read out a visceral fat level and internal body age in Japanese by female voice in a medium tone (i.e. in a tone of casual conversation).

Example 3

Figure 17:
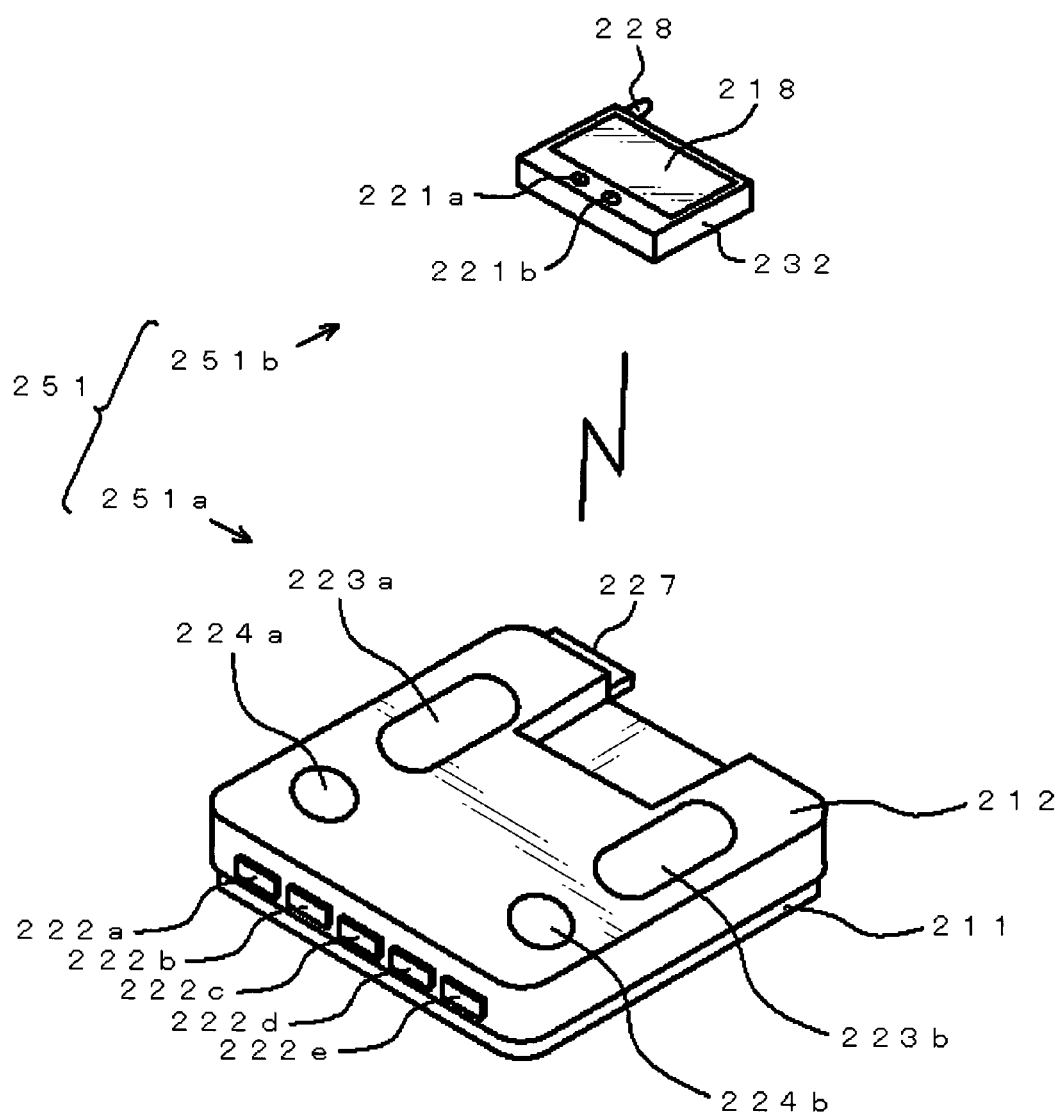
FIG. 17 is an external view of a body measuring device having an individual output format customization feature (Example 3).
Figure 18:
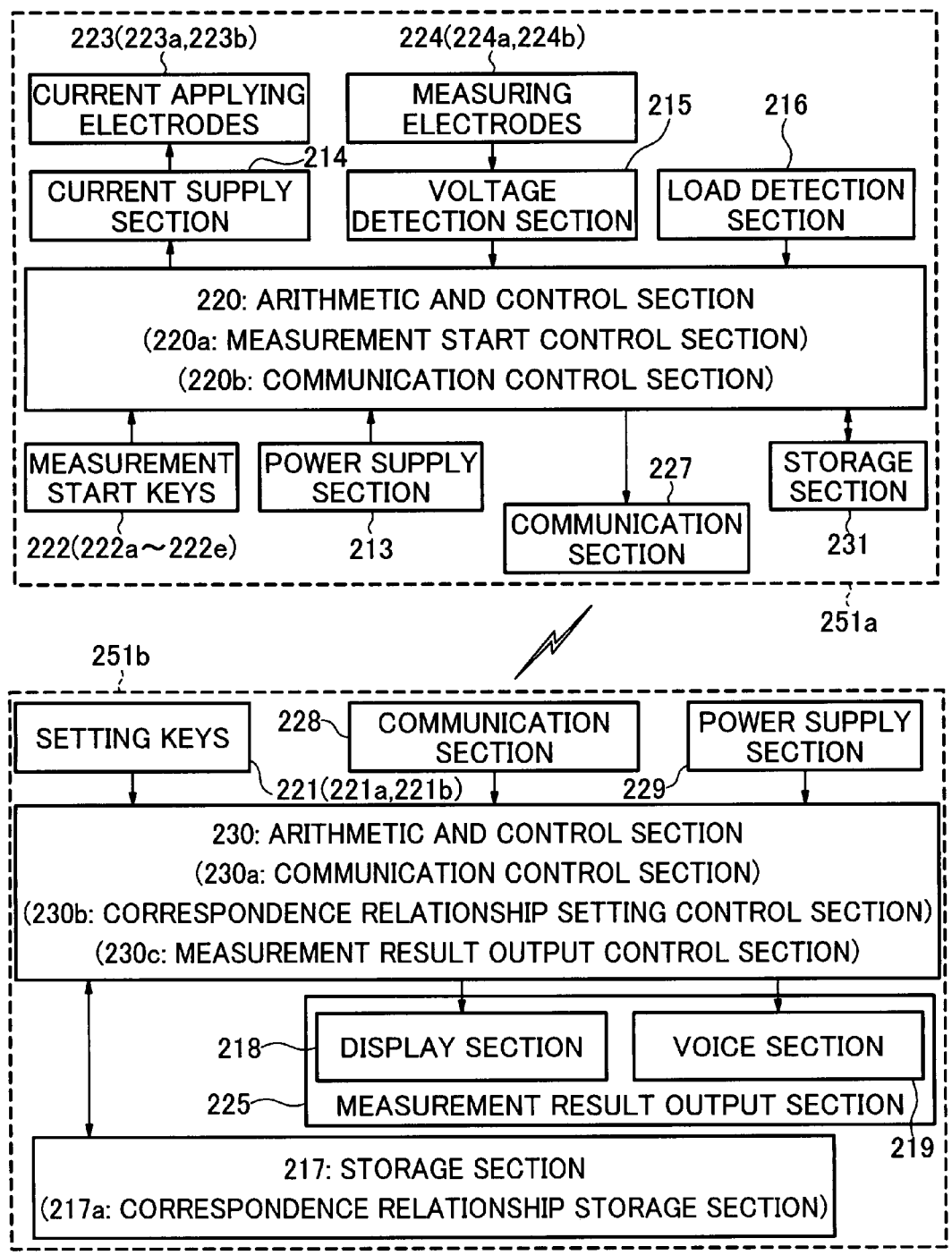
FIG. 18 is a main part block diagram which illustrates main parts constituting the body measuring device having an individual output format customization feature (Example 3).

First, the specific constitution of a body measuring device 251 having an individual output format customization feature in the present example 3 will be described by primarily using an external view shown in FIG. 17 and a main part block diagram shown in FIG. 18.

The body measuring device 251 with an individual output format customization feature in the present example 3 comprises a main unit 251a and a display box 251b. The display box 251b can be attached to and detached from the main unit 251a. Further, the main unit 251a comprises a base 211 and a platform 212. In the base 211 and platform 212, there are provided a power supply section 213, a current supply section 214, a voltage detection section 215, a load detection section 216, a storage section 231 and an arithmetic and control section 220 (measurement start control section 220a, communication control section 220b). On the external surface of the platform 212, measurement start keys 222, current applying electrodes 223, measuring electrodes 224 and a communication section 227 are provided. In addition, the display box 251*b* comprises a power supply section 229, a storage section 217 (correspondence relationship storage section 217*a*), a voice section 219 and an arithmetic and control section 230 (communication control section 230*a*, correspondence relationship setting control section 230*b*, measurement result output control section 230*c*) in a case 232. On the external surface of the case 232, setting keys 221, a communication section 228 and a display section 218 are provided.

Next, the constituents of the main unit 251*a* will be described specifically.

The power supply section 213 supplies electric power to each of the sections in the electrical system of the main unit.

The measurement start keys 222 comprise a plurality of keys 222*a*, 222*b*, 222*c*, 222*d* and 222*e*. These keys operate individually. Their individual operation causes the power supply section 213 to start supplying power for measurement.

The current supply section 214 generates a current between the current applying electrodes under the control of the arithmetic and control section 220 to pass the current through a body. The voltage detection section 215 detects a voltage generated between the measuring electrodes when a current is passed between the current applying electrodes.

The current applying electrodes 223 comprise a pair of electrodes 223*a* and 223*b* and are terminals for passing a current through a body. The measuring electrodes 224 comprise a pair of electrodes 224*a* and 224*b* and are terminals for detecting a voltage generated when a current is passed between the current applying electrodes.

The load detection section 216 comprises a weight sensor, a voltage amplifier and an A/D converter and detects a voltage generated based on a load (body weight) imposed when a subject stands on the platform 212.

The storage section 231 stores information associated with settings, measurements, calculations and display.

The communication section 227 transmits measured data obtained by the main unit 251*a* to the display box 251*b* by radio-communicating with the communication section 228 of the display box 251*b*.

The arithmetic and control section 220 also serves as the measurement start control section 220*a* and communication control section 220*b*. The arithmetic and control section 220 (i) calculates and controls a bioelectrical impedance based on a current generated from the current supply section 214 and a voltage detected by the voltage detection section 215 upon passage of the current, (ii) calculates and controls a body weight based on a detection signal from the load detection section 216 and (iii) calculates and controls various other information.

The measurement start control section 220*a* starts measurement of body indicator for each individual based on operation of each measurement start key 222. The communication control section 220*b* controls the communication section 227 to transmit data of the calculated bioelectrical impedance and body weight to the communication section 228 of the display box 251*a*.

Next, the constituents of the display box 251*b* will be described specifically.

The power supply section 229 supplies electric power to each of the sections in the electrical system of the display box 251*b*.

The setting keys 221 comprise a selection key 221*a* and an enter key 221*b*. The setting keys 221 cause the power supply section 229 to start supplying power for settings and make settings for the measurement start keys used by individuals and output formats desired by the individuals. Further, the setting keys 21 also make settings for the physical features of the individuals. More specifically, the settings of the measurement start keys are made by selecting and entering allocated numbers (Nos. 1 to 5). Meanwhile, the settings of the output formats are made by selecting whether display is needed and whether voice is needed and entering the selections. When display is needed, letter size (large, medium, small), letter color (black, red, blue, orange, green), decoration (needed or not needed; if needed, decorations a to d), display items (body fat percentage, body weight, visceral fat level, muscle mass, body water content, basal metabolic rate, bone mass, internal body age), language (Japanese, English, French, German, Chinese, Korean), graph (line, bar) and advice (needed or not needed) are selected and entered. When voice is needed, voice volume (large, medium, small), gender (male, female), language (Japanese, English, French, German, Chinese, Korean) and voice items (body fat percentage, body weight, visceral fat level, muscle mass, body water content, basal metabolic rate, bone mass, internal body age) are selected and entered. Further, the settings of the physical features are made by selecting and entering gender (male, female), age (0 to 100) and height (10 to 250 cm).

The communication section 228 receives measured data from the main unit 251*a* by radio-communicating with the communication section 227 of the main unit 251*a*.

The storage section 217 also serves as the correspondence relationship storage section 217*a* and stores information associated with settings, measurements, calculations and display.

The correspondence relationship storage section 217*a* stores correspondence relationships between the measurement start keys 222 used by individuals and output formats desired by the individuals and correspondence relationships between the measurement start keys 222 used by the individuals and the physical features of the individuals.

The display section 218 displays items associated with settings made by the setting keys 221 and displays the measurement results of body indicators (body weight value, body fat percentage, visceral fat level, muscle mass, body water content, basal metabolic rate, bone mass, internal body age) calculated by the arithmetic and control section 220 in a predetermined output format.

The voice section 219 reads out the measurement results of body indicators (body weight value, body fat percentage, visceral fat level, muscle mass, body water content, basal metabolic rate, bone mass, internal body age) calculated by the arithmetic and control section 220 in a predetermined output format.

The display section 218 and the voice section 219 constitute a measurement result output section 225.

The arithmetic and control section 230 also serves as the communication control section 230*a*, correspondence relationship setting control section 230*b* and measurement result output control section 230*c*. The arithmetic and control section 230 (i) controls setting of physical features by the setting keys 221, (ii) selects physical features corresponding to a measurement start key 222 which has caused the measurement start control section 220*a* to start measurement of body indicator from the correspondence relationships between the measurement start keys 222 used by individuals and the physical features of the individuals and calculates and controls body indicators (body weight value, body fat percentage, visceral fat level, muscle mass, body water content, basal metabolic rate, bone mass, internal body age) based on the selected physical features and the calculated bioelectrical impedance, and (iii) calculates and controls various other information.

The communication control section 230*a* controls the communication section 228 to receive data of the bioelectrical impedance and body weight which has been transmitted from the communication section 227 of the main unit 251a. The correspondence relationship setting control section 230b sets correspondence relationships between the measurement start keys 222 used by individuals and output formats desired by the individuals which have been set by the setting keys 221 and sets correspondence relationships between the measurement start keys 222 used by individuals and the physical features of the individuals. The measurement result output control section 230c selects an output format corresponding to a measurement start key 222 which has caused the measurement start control section 220a to start measurement of body indicator from the correspondence relationships between the measurement start keys 222 used by individuals and the output formats desired by the individuals which have been stored in the correspondence relationship storage section 217a and controls output of the result of measurement of the body indicator in the selected output format.

The measurement start keys 222 and the measurement start control section 220a constitute the individual measurement start means 1. Further, the setting keys 221, the correspondence relationship setting control section 230b and the correspondence relationship storage section 217a constitute the individual output format customization means 3. In addition, the measurement result output control section 230c and the measurement result output section 225 constitute the individual measurement result output means 4.

Next, the operations of the body measuring device 251 with an individual output format customization feature in the present example 3 will be described. The operations at the time of setting in the present example 3 are the same as those described by use of the setting flowchart of FIG. 4 in the present example 1 except that the base 11, platform 12, power supply section 13, current supply section 14, voltage detection section 15, load detection section 16, storage section 17, correspondence relationship storage section 17a, display section 18, voice section 19, arithmetic and control section 20, measurement start control section 20a, correspondence relationship setting control section 20b, measurement result output control section 20c, settings keys 21, measurement start keys 22, current applying electrodes 23 and measuring electrodes 24 in Example 1 are replaced by the base 211, platform 212, power supply section 229, current supply section 214, voltage detection section 215, load detection section 216, storage section 217, correspondence relationship storage section 217a, display section 218, voice section 219, arithmetic and control section 230, measurement start control section 220a, correspondence relationship setting control section 230b, measurement result output control section 230c, settings keys 221, measurement start keys 222, current applying electrodes 223 and measuring electrodes 224 in Example 3. Accordingly, descriptions thereof will be omitted.

The operations at the time of measurement in the present example 3 will be described by primarily using the measurement flowchart shown in FIG. 5, as in the description in Example 1.

First, when the measurement start key 222 which has been set for a subject is pressed, the power supply section 213 supplies electric power to each of the sections in the electrical system of the main unit 251a. Further, the power supply section 229 of the display box 251b constantly supplies electric power to each of the sections in the electrical system of the display box 251b. Then, when the subject stands on the platform 212 with the bottom of the left foot in contact with the current applying electrode 223a and the measuring electrode 224a and the bottom of the right foot in contact with the current applying electrode 223b and the measuring electrode 224b, the load detection section 216 detects a voltage generated at that time, the arithmetic and control section 220 calculates the body weight of the subject, and the storage section 231 stores the calculated body weight. Then, the arithmetic and control section 220 calculates a bioelectrical impedance based on a current generated from the current supply section 214 and a voltage detected at that time by the voltage detection section 215, and the storage section 231 stores the calculated bioelectrical impedance.

Then, under the control of the communication control section 220b, the communication section 227 transmits the body weight and bioelectrical impedance stored in the storage section 231 to the communication section 228 of the display box 215b.

Then, the arithmetic and control section 230 of the display box 251b calculates the body fat percentage, visceral fat level, muscle mass, body water content, basal metabolic rate, bone mass and/or internal body age which have/has been set as the display item(s) and the voice item(s) based on the body weight and bioelectrical impedance received by the communication section 228 and physical features corresponding to the allocated number of the measurement start key 222 for the subject from the above stored correspondence relationship between the allocated number and the physical features (STEP S11). For example, when a body fat percentage, body weight, basal metabolic rate and bone mass are set as the display items as shown in FIG. 10 and a visceral fat level and internal body age are set as the voice items as shown in FIG. 12, the body fat percentage, visceral fat level, basal metabolic rate, bone mass and internal body age are calculated.

Then, the measurement result output control section 230c selects an output format corresponding to the allocated number of the measurement start key 222 for the subject from the correspondence relationship between the allocated number and the output format which has been stored in the correspondence relationship storage section 217a and controls the display section 218 and the voice section 219 to output the body fat percentage, body weight, visceral fat level, muscle mass, body water content, basal metabolic rate, bone mass and/or internal body age which have/has been calculated as the display item(s) and the voice item(s) in this selected output format. Then, the display section 218 displays the data under the control of the control section 230c, and the voice section 219 reads out the data under the control of the control section 220c (STEP S12), thereby ending a series of measurements. For example, when the display items and the voice items are set as shown in FIGS. 8, 10 and 12, the display section 218 displays a measurement result screen as shown in FIG. 13(e), and the voice section 219 reads out a visceral fat level and internal body age in Japanese by female voice in a medium tone (i.e. in a tone of casual conversation).

Example 4

Figure 19:
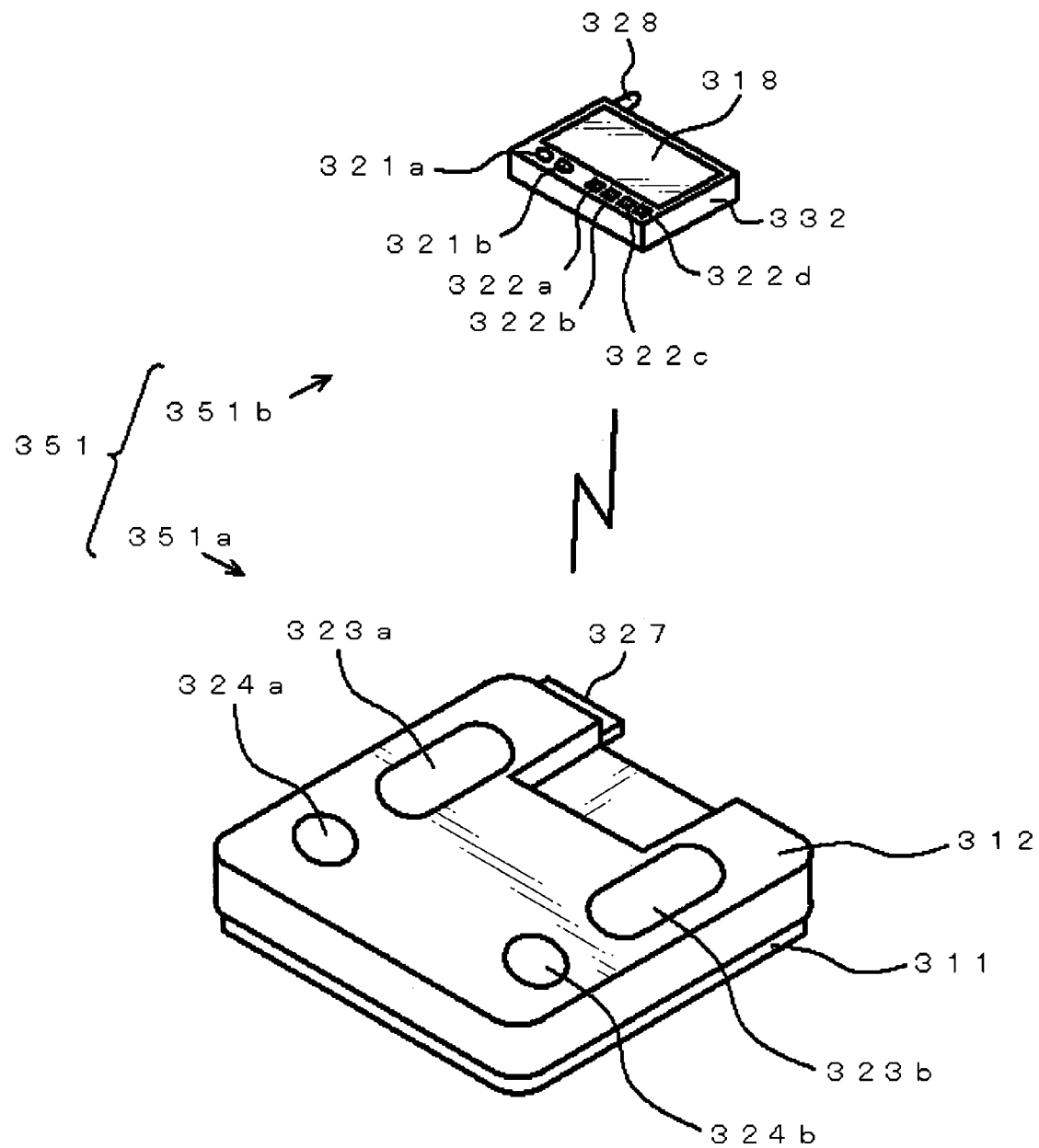
FIG. 19 is an external view of a body measuring device having an individual output format customization feature (Example 4).
Figure 20:
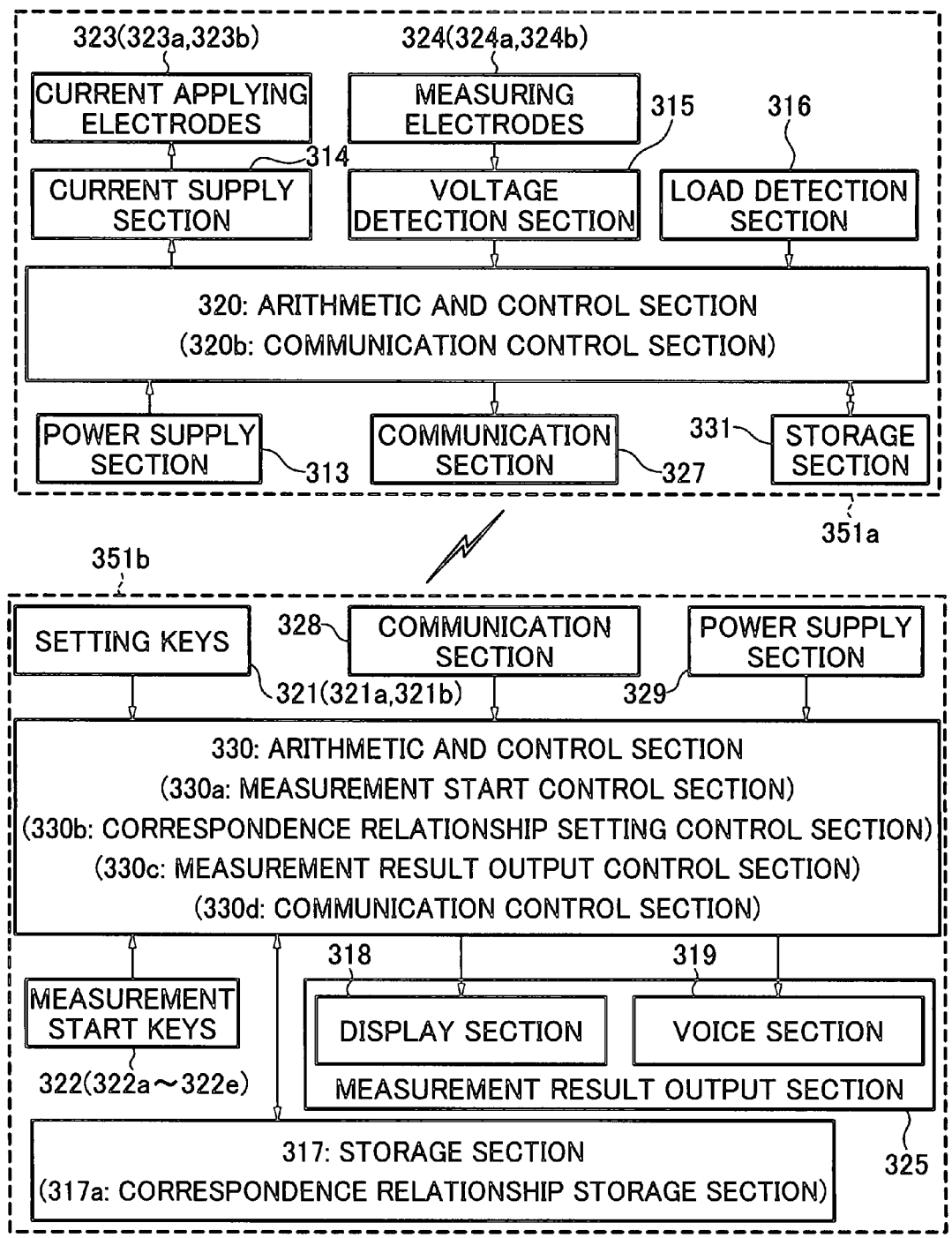
FIG. 20 is a main part block diagram which illustrates main parts constituting the body measuring device having an individual output format customization feature (Example 4).

First, the specific constitution of a body measuring device 351 having an individual output format customization feature in the present example 4 will be described by primarily using an external view shown in FIG. 19 and a main part block diagram shown in FIG. 20.

The body measuring device 351 with an individual output format customization feature in the present example 4 comprises a main unit 351a and a display box 351b. The display box 351b can be attached to and detached from the main unit 351a. Further, the main unit 351a comprises a base 311 and a platform 312. In the base 311 and platform 312, there are provided a power supply section 313, a current supply section 314, a voltage detection section 315, a load detection section 316, a storage section 331 and an arithmetic and control section 320 (communication control section 320b). On the external surface of the platform 312, current applying electrodes 323, measuring electrodes 324 and a communication section 327 are provided. In addition, the display box 351b comprises a power supply section 329, a storage section 317 (correspondence relationship storage section 317a), an arithmetic and control section 330 (measurement start control section 330a, correspondence relationship setting control section 330b, measurement result output control section 330c, communication control section 330d) and a voice section 319 in a case 332. On the external surface of the case 332, setting keys 321, measurement start keys 322, a communication section 328 and a display section 318 are provided.

The base 311, power supply section 313, current supply section 314, voltage detection section 315, load detection section 316, current applying electrodes 323, measuring electrodes 324, storage section 331, communication section 328, power supply section 329, setting keys 321, storage section 317 (correspondence relationship storage section 317a), display section 318 and voice section 319 correspond to the base 211, power supply section 213, current supply section 214, voltage detection section 215, load detection section 216, current applying electrodes 223, measuring electrodes 224, storage section 217, communication section 328, power supply section 329, setting keys 321, storage section 317 (correspondence relationship storage section 317a), display section 318 and voice section 319 in Example 3 and serve in the same way as their counterparts in Example 3.

The arithmetic and control section 320 also serves as the communication control section 320b. The arithmetic and control section 320 (i) calculates and controls a bioelectrical impedance based on a current generated from the current supply section 314 and a voltage detected by the voltage detection section 315 upon passage of the current, (ii) calculates and controls a body weight based on a detection signal from the load detection section 316 and (iii) calculates and controls various other information.

The measurement start keys 322 comprise a plurality of keys 322a, 322b, 322c, 322d and 322e. These keys operate individually. Their individual operation causes the power supply section 329 to start supplying power for measurement.

The arithmetic and control section 330 also serves as the measurement start control section 330a, correspondence relationship setting control section 330b, measurement result output control section 330c and communication control section 330d. The arithmetic and control section 330 (i) controls setting of physical features by the setting keys 321, (ii) selects physical features corresponding to a measurement start key 322 which has caused the measurement start control section 320a to start measurement of body indicator from the correspondence relationships between the measurement start keys 322 used by individuals and the physical features of the individuals and calculates and controls body indicators (body weight value, body fat percentage, visceral fat level, muscle mass, body water content, basal metabolic rate, bone mass, internal body age) based on the selected physical features and the calculated bioelectrical impedance, and (iii) calculates and controls various other information.

The measurement start keys 322 and the measurement start control section 320a constitute the individual measurement start means 1. Further, the setting keys 321, the correspondence relationship setting control section 330b and the correspondence relationship storage section 317a constitute the individual output format customization means 3. In addition, the measurement result output control section 330c and the measurement result output section 325 constitute the individual measurement result output means 4.

Next, the operations of the body measuring device 351 with an individual output format customization feature in the present example 4 will be described. The operations at the time of setting in the present example 4 are the same as those described by use of the setting flowchart of FIG. 4 in the present example 1 except that the base 11, platform 12, power supply section 13, current supply section 14, voltage detection section 15, load detection section 16, storage section 17, correspondence relationship storage section 17a, display section 18, voice section 19, arithmetic and control section 20, measurement start control section 20a, correspondence relationship setting control section 20b, measurement result output control section 20c, settings keys 21, measurement start keys 22, current applying electrodes 23 and measuring electrodes 24 in Example 1 are replaced by the base 311, platform 312, power supply section 329, current supply section 314, voltage detection section 315, load detection section 316, storage section 317, correspondence relationship storage section 317a, display section 318, voice section 319, arithmetic and control section 330, measurement start control section 320a, correspondence relationship setting control section 330b, measurement result output control section 330c, settings keys 321, measurement start keys 322, current applying electrodes 323 and measuring electrodes 324 in Example 4. Accordingly, descriptions thereof will be omitted.

The operations at the time of measurement in the present example 4 will be described by primarily using the measurement flowchart shown in FIG. 5, as in the description in Example 1.

First, when the measurement start key 322 which has been set for a subject is pressed, the power supply section 329 supplies electric power to each of the sections in the electrical system of the display box 351b. Further, the power supply section 313 of the main unit 351a constantly supplies electric power to each of the sections in the electrical system of the main unit 351a. Then, when the subject stands on the platform 312 with the bottom of the left foot in contact with the current applying electrode 323a and the measuring electrode 324a and the bottom of the right foot in contact with the current applying electrode 323b and the measuring electrode 324b, the load detection section 316 detects a voltage generated at that time, the arithmetic and control section 320 calculates the body weight of the subject, and the storage section 331 stores the calculated body weight. Then, the arithmetic and control section 320 calculates a bioelectrical impedance based on a current generated from the current supply section 314 and a voltage detected at that time by the voltage detection section 315, and the storage section 331 stores the calculated bioelectrical impedance.

Then, under the control of the communication control section 320b, the communication section 327 transmits the body weight and bioelectrical impedance stored in the storage section 331 to the communication section 328 of the display box 351b.

Then, the arithmetic and control section 330 of the display box 351b calculates the body fat percentage, visceral fat level, muscle mass, body water content, basal metabolic rate, bone mass and/or internal body age which have/has been set as the display item(s) and the voice item(s) based on the body weight and bioelectrical impedance received by the communication section 328 and physical features corresponding to the allocated number of the measurement start key 322 for the subject from the above stored correspondence relationship between the allocated number and the physical features (STEP S11). For example, when a body fat percentage, body weight, basal metabolic rate and bone mass are set as the display items as shown in FIG. 10 and a visceral fat level and internal body age are set as the voice items as shown in FIG. 12, the body fat percentage, visceral fat level, basal metabolic rate, bone mass and internal body age are calculated.

Then, the measurement result output control section 330c selects an output format corresponding to the allocated number of the measurement start key 322 for the subject from the correspondence relationship between the allocated number and the output format which has been stored in the correspondence relationship storage section 317a and controls the display section 318 and the voice section 319 to output the body fat percentage, body weight, visceral fat level, muscle mass, body water content, basal metabolic rate, bone mass and/or internal body age which have/has been calculated as the display item(s) and the voice item(s) in this selected output format. Then, the display section 318 displays the data under the control of the control section 330c, and the voice section 319 reads out the data under the control of the control section 330c (STEP S12), thereby ending a series of measurements. For example, when the display items and the voice items are set as shown in FIGS. 8, 10 and 12, the display section 318 displays a measurement result screen as shown in FIG. 13(e), and the voice section 319 reads out a visceral fat level and internal body age in Japanese by female voice in a medium tone (i.e. in a tone of casual conversation).

The thus constituted body measuring device having an individual output format customization feature of the present example can inform a number of subjects who use the device of measurement results of body indicators in output formats desired by the individual subjects. For example, when the present device is used by a family comprising a grandmother, father, mother, son and daughter, the grandmother, father, mother, son and daughter can be provided with measurement result screens displayed in different output formats shown in FIGS. 13(c), 13(a), 13(b), 13(d) and 13(e), respectively, by registering their desired output formats with the measurement start keys Nos. 3, 1, 2, 4 and 5 before measurement, respectively.

What is claimed is:

1. A body measuring device having an individual output format customization feature, comprising:
    individual measurement start means,
    body measurement means,
    individual output format customization means, and
    individual measurement result output means,
    wherein
    the individual measurement start means starts measurement of only a selected body indicator for an individual subject, out of a plurality of body indicators,
    the body measurement means measures the body indicator for the individual based on the start by the individual measurement start means,
    the individual output format customization means customizes, for the individual, an output format for the result of measurement of the selected body indicator, and
    the individual measurement result output means outputs the result of measurement of only the selected body indicator for the individual by the body measurement means, in the output format customized for the individual by the individual output format customization means.

2. The body measuring device of claim 1, wherein
    the individual measurement start means comprises:
    a plurality of measurement start keys which operate individually, and
    a measurement start control section which starts measurement of a body indicator for the individual based on the operation of each measurement start key,
    the individual output format customization means comprises:
    setting keys which set the measurement start keys used by the individual and output formats desired by the individual,
    a correspondence relationship setting control section which sets correspondence relationships between the measurement start keys used by the individual and the output formats desired by the individual which have been set by the setting keys, and
    a correspondence relationship storage section which stores the correspondence relationships set by the correspondence relationship setting control section, and
    the individual measurement result output means comprises:
    a measurement result output control section which selects an output format corresponding to a measurement start key which has caused the measurement start control section to start measurement of the body indicator and controls output of the result of measurement of the body indicator in the selected output format, and
    a measurement result output section which outputs the result of measurement of the body indicator under the control of the measurement result output control section.

3. The body measuring device of claim 2, wherein
    the output format includes a display item and/or a voice item, and
    the body measurement means measures only a body indicator associated with a display item and/or a voice item which have/has been set by the setting keys.

4. The body measuring device of claim 1, wherein the output format customization means customizes the output format responsive to instructions from the individual.

5. The body measuring device of claim 4, wherein
    the output format includes a display item and/or a voice item, and
    the body measurement means measures only a body indicator associated with the display item and/or the voice item.

6. The body measuring device of claim 5, wherein the display item includes at least one of body fat percentage, body weight, visceral fat level, muscle mass, body water content, basal metabolic rate, bone mass, and internal body age.

7. The body measuring device of claim 5, wherein the voice item includes at least one of body fat percentage, body weight, visceral fat level, muscle mass, body water content, basal metabolic rate, bone mass, and internal body age.

8. The body measuring device of claim 1, wherein the plurality of body indicators includes at least one of body fat percentage, body weight, visceral fat level, muscle mass, body water content, basal metabolic rate, bone mass, and internal body age.

9. The body measuring device of claim 5, wherein the display item includes a decoration.

10. The body measuring device of claim 5, wherein the display item includes a graph relating to the selected body indicator.

11. The body measuring device of claim 5, wherein the display item includes advice relating to the selected body indicator.

* * * * *